(12) United States Patent
Nettesheim et al.

(10) Patent No.: US 10,004,914 B2
(45) Date of Patent: Jun. 26, 2018

(54) ASSEMBLY FOR THE TREATMENT OF WOUNDS

(71) Applicant: relyon plasma GmbH, Regensburg (DE)

(72) Inventors: Stefan Nettesheim, Regensburg (DE); Dariusz Korzec, Wenzenbach (DE); Dominik Burger, Alteglofsheim (DE)

(73) Assignee: reylon plasma GmbH, Regensburg (DE)

( * ) Notice: Subject to any disclaimer, the term of this patent is extended or adjusted under 35 U.S.C. 154(b) by 84 days.

(21) Appl. No.: 15/177,931

(22) Filed: Jun. 9, 2016

(65) Prior Publication Data

US 2016/0287892 A1    Oct. 6, 2016

Related U.S. Application Data

(63) Continuation of application No. PCT/IB2014/066808, filed on Dec. 11, 2014.

(30) Foreign Application Priority Data

Dec. 12, 2013  (DE) .................. 10 2013 113 905

(51) Int. Cl.
*A61M 37/00*   (2006.01)
*A61N 1/44*    (2006.01)
(Continued)

(52) U.S. Cl.
CPC .......... *A61N 1/44* (2013.01); *A61F 13/00059* (2013.01); *A61F 13/02* (2013.01);
(Continued)

(58) Field of Classification Search
CPC ............... A61F 13/00059; A61F 13/02; A61L 2202/11; A61L 2202/16; A61L 2/0011;
(Continued)

(56) References Cited

U.S. PATENT DOCUMENTS 3,712,298  A  *  1/1973  Snowdon ............. A61H 9/0071
                                               601/11
2010/0296977 A1*  11/2010 Hancock .................. A61L 2/14
                                               422/186
(Continued)

FOREIGN PATENT DOCUMENTS

DE     102011001416    9/2012
DE     102013107448    1/2015
(Continued)

*Primary Examiner* — Jason Flick
(74) *Attorney, Agent, or Firm* — Simpson & Simpson, PLLC

(57) ABSTRACT

An assembly for the treatment of wounds comprising a device for generating a plasma, or an excited gas or gas mixture, respectively. A covering is used to cover a wound area. A first conduit connects the device and the covering and a second conduit connects the covering and a pump. The device is arranged within a housing comprising an opening. The device comprises a piezoelectric transformer having a high-voltage end for generating the plasma, and is arranged within the housing such that the high-voltage end is directed towards the opening. The plasma or the excited gas or gas mixture, respectively, is generated in a region of the opening of the housing. A wound cover comprising a means for guiding the plasma across the wound area is arranged between the covering and the wound area.

16 Claims, 4 Drawing Sheets

(51) Int. Cl.
*A61N 1/04* (2006.01)
*A61L 2/14* (2006.01)
*A61F 13/00* (2006.01)
*A61F 13/02* (2006.01)
*A61L 2/00* (2006.01)
*H05H 1/24* (2006.01)

(52) U.S. Cl.
CPC ............ *A61L 2/0011* (2013.01); *A61L 2/14* (2013.01); *A61N 1/0468* (2013.01); *A61L 2202/11* (2013.01); *A61L 2202/16* (2013.01); *H05H 2001/2481* (2013.01)

(58) Field of Classification Search
CPC ........... A61L 2/14; A61N 1/0468; A61N 1/44; H05H 2001/2481
USPC ......................................................... 604/23
See application file for complete search history.

(56) References Cited

U.S. PATENT DOCUMENTS

2013/0144280 A1* 6/2013 Eckhouse ............... A45D 26/00
606/9
2013/0226073 A1 8/2013 Kummerfeld et al.

FOREIGN PATENT DOCUMENTS

| EP | 2170022 | 3/2010 |
|---|---|---|
| EP | 2251059 | 11/2010 |
| EP | 2445320 | 4/2012 |
| EP | 2599506 | 6/2013 |
| WO | 2010/034451 | 4/2010 |
| WO | 2011/110191 | 9/2011 |
| WO | 2011/138463 | 11/2011 |
| WO | 2013/093868 | 6/2013 |

* cited by examiner

ASSEMBLY FOR THE TREATMENT OF WOUNDS

CROSS-REFERENCE TO RELATED APPLICATIONS

This application is filed under 35 U.S.C. §§ 111(a) and 365(c) as a continuation of International Patent Application No. PCT/IB2014/066808, filed Dec. 11, 2014, which application claims the priority from German Patent Application No. 10 2013 113 905.1, filed Dec. 12, 2013, which applications are incorporated herein by reference in their entirety.

TECHNICAL FIELD

The invention relates to an assembly for the treatment of wounds by guiding plasma or an excited gas or gas mixture, respectively, over a wound area. More specifically, a generated plasma or an excited gas or gas mixture, respectively, is pumped through a wound covering to treat a wound.

BACKGROUND

The not yet published German patent application DE 10 2013 107 448.0 discloses an apparatus for the reduction of germs by means of plasma. The dielectric film encloses an area to be sterilized (wound or object) with its peripheral edge. A high voltage end of the piezoelectric transformer is facing the outside of the dielectric film and the plasma is ignited within the dielectric film.

The international patent application WO 2010/034451 A1 discloses a plasma applicator for applying a non-thermal plasma to a surface, in particular for the plasma treatment of living tissue and in particular for the plasma treatment of wounds. The plasma applicator includes a cover lid for covering a part of the surface. In this way, a cavity is formed between the cover lid and the surface. The non-thermal plasma is provided in the cavity, and in addition, the cavity can be flushed with gas. Likewise a pump is provided which extracts gas from the cavity.

The international patent application WO 2013/093868 A1 discloses an apparatus for selective activation for medical implants by means of plasma, and an apparatus for wound healing. A plasma is guided from a plasma generator to a moveable applicator or head by means of a flexible hose. The plasma is directed onto an implant via openings in a template.

The German patent application DE 10 2011 001 416 A1 discloses a plasma treatment apparatus for treating wounds or afflicted portions of skin. The plasma treatment apparatus has two flexible area electrodes for generating a non-thermal plasma. The two area electrodes each include at least one electric conductor, wherein the conductors are interwoven. At the outside of the area electrodes, facing the surface to be treated, a wound contact layer of an antiseptically treated material is detachably fixed.

SUMMARY OF THE INVENTION

It is an object of the invention to provide an assembly for the treatment of wounds which is cost-efficient, easy to use, and by which an efficient and safe treatment of wounds is achieved. This object is achieved by an assembly for the treatment of wounds, which has a device for generating a plasma or an excited gas or gas mixture, respectively. A covering is used to cover a wound area to be treated. A first conduit supplies the plasma or the excited gas mixture from the device to the covering for the wound area to be treated. A second conduit leads from the covering for the wound area to be treated to a pump. The device has a housing wherein an opening is formed in the housing. A piezoelectric transformer of the device has a high-voltage end for generating the plasma or the excited gas or gas mixture, respectively. The piezoelectric transformer is arranged in the housing such that the high-voltage end of the piezoelectric transformer is directed towards the opening in the housing. The plasma or the excited gas or gas mixture, respectively, is generated in a region of the opening of the housing.

The covering for the wound area to be treated is glued with its circumferential edge to the body part, i.e., the skin, or connected in such a way, respectively, that the circumferential edge of the covering encloses the wound area to be treated. An electronic coupling may be provided between the pump and the device. The coupling may be wired or wireless, and advantageously, the pump and the device can be easily adapted to each other in such a way that an effective wound treatment can be carried out. Likewise, unnecessary stress for the patient caused by, for example, a prolonged or highly dosed treatment with the plasma or the excited gas or gas mixture, respectively, is avoided. If a plasma is generated with the device, the device can aspirate ambient air directly or via a filter.

Likewise, process gas may be supplied to the device for generating a plasma or an excited gas or gas mixture, respectively, in a defined manner via a line. The device may be a plasma generator, or an ionizer, or an ozonizer. In case the device is an ionizer or ozonizer, instead of a plasma, a gas mixture with excited molecules, ions and reactive oxygen species, like for example ozone, atomic oxygen, H2O2, OH-radicals, or $NO_x$ affects the wound area. Strictly speaking it is not necessary for a plasma to reach the wound area.

The plasma, or the excited gas or gas mixture, generated in the device is guided to the covering by means of a first conduit. The covering has at least a supply port and at least a removal port. The first conduit is connected with the supply port, and the second conduit, towards the pump, is connected with the removal port. The first conduit has a connection element which is removably connectable with the opening of the housing. In this way, the plasma or the excited gas or gas mixture, respectively, directly enters the first conduit from the device.

With regard to the covering, a wound cover is provided between the covering and the wound area to be treated. A means is provided within the wound cover for guiding the plasma or the excited gas or gas mixture, respectively, through the wound cover, and for efficiently affecting the wound area to be treated. The means is such that a guiding of the plasma or of the excited gas or gas mixture, respectively, from the supply port to the removal port is achieved. The plasma or the excited gas or gas mixture, respectively, therein is guided on a path from the supply port to the removal port across or to, respectively, the wound area to be treated.

The means for guiding the plasma or the excited gas or gas mixture, respectively, may come in various embodiments. The means for guiding the plasma or the excited gas or gas mixture, respectively, may, for example, include a plurality of straight distribution channels, leading from a distribution element to a collection element. The distribution element is connected to the supply port, and the collection element is connected to the removal port. The plurality of straight conduits are embedded into the wound cover in such a way that, from the distribution channels, the exiting plasma or the excited gas or gas mixture, respectively, affects the wound to be treated.

According to another embodiment, the means for guiding the plasma or the excited gas or gas mixture, respectively, is configured as a single meandering distribution channel, directly connected to the supply port and the removal port.

According to yet another embodiment, the means for guiding the plasma, or the excited gas, or gas mixture, respectively, includes a plurality of flow obstacles. The flow obstacles are distributed in the wound cover according to a regular lattice and are arranged between a distribution element and a collection element. The distribution element is connected to the supply port, and the collection element is connected to the removal port. The plasma, or the excited gas, or gas mixture, respectively, exits from the distribution element and moves through the wound cover due to the pump action at the collection element. The flow obstacles advantageously provide a uniform distribution of the plasma, or the excited gas, or gas mixture, respectively, within the wound cover.

According to a further embodiment, the means for guiding the plasma, or the excited gas, or gas mixture, respectively, includes a plurality of distribution channels, each provided with two redirections. The lines lead from the distribution element to the collection element. The distribution element in turn is connected with the supply port and the collection element is connected with the removal port. In case the distribution element and the collection element are arranged outside of the covering, the lines protruding from the covering are connected with the distribution element and the collection element, respectively.

According to yet a further embodiment, the means for guiding the plasma, or the excited gas, or gas mixture, respectively, is formed as a structure with open pores. The structure with open pores is facing the wound area to be treated.

The wound cover has a thickness of, for example, 3 mm and the distribution channels have a depth of about 1.5 mm, and are open towards the wound area. Typically, the distribution channels can also be referred to as the gas distributor or "flow-field." Instead of the gas distributor structured in an ordered manner, the gas distributor may also be a structure with pores open towards the wound area.

In order to keep the distribution channels or the gas distributor, respectively, free of liquid, they may comprise a hydrophobic coating. A particularly suitable method of manufacturing the distribution channels is to emboss them into the wound cover.

A color sensor may also be assigned to the covering in order to indicate, by a change of color, that the treatment is completed. Furthermore, an RFID-chip may be assigned to the covering so that, via the type of the covering and in connection with the device and pump, at least a duration of the treatment is settable. By means of the RFID-chip it is possible to adjust the device and pump in such a manner that at least the strength and the duration of the generated plasma or of the excited gas or gas mixture and, as the case may be, the supply of additional gas such as, for example, argon, are adapted to the type of the covering.

According to a possible embodiment the device is a plasma generation device with a piezoelectric transformer for generating the plasma. The high-voltage end of the piezoelectric transformer is directed towards the opening in the housing. The plasma generation device is configured as a hand-held device.

It is advantageous that the device is a hand-held device. The hand-held device is cost-efficient and assures easy handling. In combination with the stationary covering, a safe and efficient treatment of the wound is possible despite the hand-held device. Furthermore, the covering, the wound cover, and the means for guiding the plasma can be manufactured in a simple and cost-efficient manner and in various configurations.

BRIEF DESCRIPTION OF THE DRAWINGS

Further advantages and advantageous embodiments of the invention are the subject of the following figures and their corresponding description, in which.

DETAILED DESCRIPTION OF THE INVENTION

Identical reference signs are used for like elements of the invention or elements of like function. The embodiments shown are only a possibility of how the assembly for treatment of wounds by means of a generated plasma may be configured. Although the following description refers exclusively to a device configured as a plasma generation device, this is not to be taken as a limitation of the invention. As already mentioned above, instead of a plasma, a gas mixture with excited molecules, ions, and reactive oxygen species, like for example ozone, atomic oxygen, $H_2O_2$, OH-radicals, or NOx may bring about the effects at the treatment of wounds. Strictly speaking, it is not necessary for plasma to reach the wound area.

Figure 1:
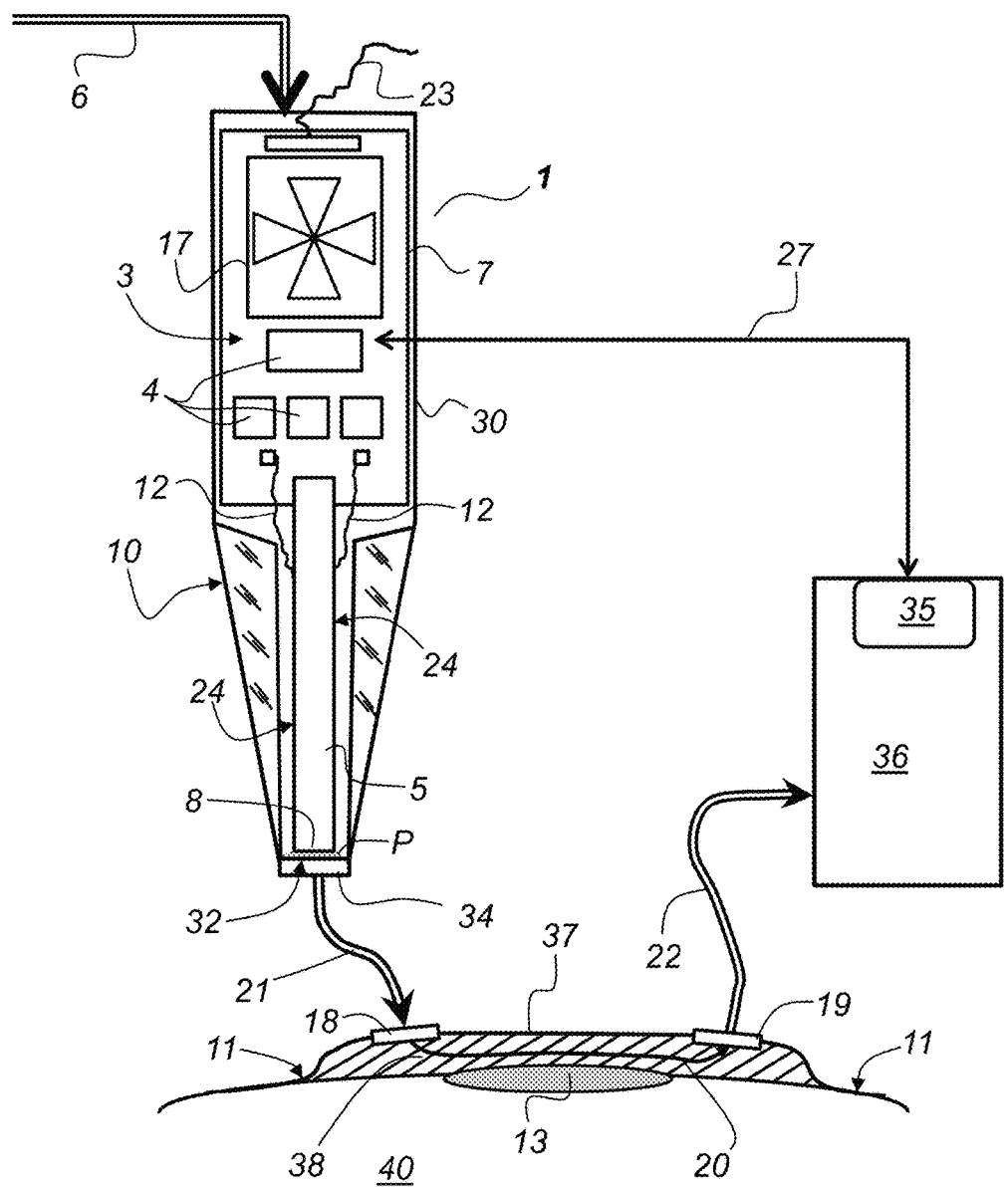
FIG. 1 is a schematic view of the principal configuration of the assembly for the plasma treatment of wounds according to the invention.

FIG. 1 is a schematic view of assembly 1 for the treatment of wounds according to an embodiment of the invention. Plasma P is generated in plasma generation device 10 with piezoelectric transformer 5. Piezoelectric transformer 5 is arranged in housing 30 of plasma generation device 10. Although the following description refers to piezoelectric transformer 5, this is not to be taken as a limitation of the invention and it should be appreciated that plasma P may be generated by any other suitable means, as is obvious to a person having ordinary skill in the art. For control, piezoelectric transformer 5 is connected with circuit board 7. Circuit board 7 implements control circuit 3 by a plurality of electronic elements 4. By means of control circuit 3, it is possible to excite piezoelectric transformer 5 at its resonance frequency. Control circuit 3 for piezoelectric transformer 5 may be connected to an external power supply, which is a standard mains-adapter (not shown), connected via cable 23 with housing 30 of piezoelectric transformer 5. Likewise, the power supply can be an accumulator. A combination of an accumulator and standard mains-adapter is also conceivable. The control voltage is applied to a respective side surface 24 of piezoelectric transformer 5 via respective electrical contact 12 by control circuit 3 of circuit board 7. Due to the excitation voltage applied to side surfaces 24 of piezoelectric transformer 5, the required high voltage is generated at high-voltage end 8 of the piezoelectric transformer 5. Furthermore, fan 17 may be provided in or at housing 30, which provides a flow of air in housing 30 towards opening 32 of housing 30. Likewise, a gas or a gas mixture may be supplied to plasma generation device 10 via gas line 6, with which the plasma is ignited above piezoelectric transformer 5.

Wound area 13 is the area on body part 40 to be treated. Covering 37 encloses wound area 13 and is glued to body part 40 at circumferential edge 11. Wound cover 38 is provided between covering 37 and wound area 13. Furthermore, covering 37 has at least one supply port 18 and at least one removal port 19.

Plasma P is transported from plasma generation device 10 to supply port 18 by means of first conduit 21. First conduit 21 is connected to plasma generation device 10 via connection element 34. To this end, connection element 34 is removably connected to opening 32 of housing 30.

Second conduit 22 leads from at least one removal port 19 of covering 37 to pump 36. Pump 36 directs the flow of plasma P across wound area 13 within wound cover 38. An optimal and efficient treatment of wound area 13 may be achieved by a specific adjustment of the power of pump 36 (i.e., flow rate of plasma P) and the power of plasma generation device 10 (i.e., volume of plasma P generated). The specific adjustment may be achieved by coupling 27, which electrically couples pump 36 with plasma generation device 10. Coupling 27 is an electronic coupling device and may be wireless or wired. Control circuit 35 of pump 36 and control circuit 3 of plasma generation device 10 thus can adjust the settings of assembly 1 to achieve efficient and successful treatment of a wound. Additionally, means 25 is provided within wound cover 38 by which plasma P is guided from supply port 18 to removal port 19 (see FIGS. 2-5). Plasma P is therefore guided across wound area 13 on a path from supply port 18 to removal port 19.

Figure 2:
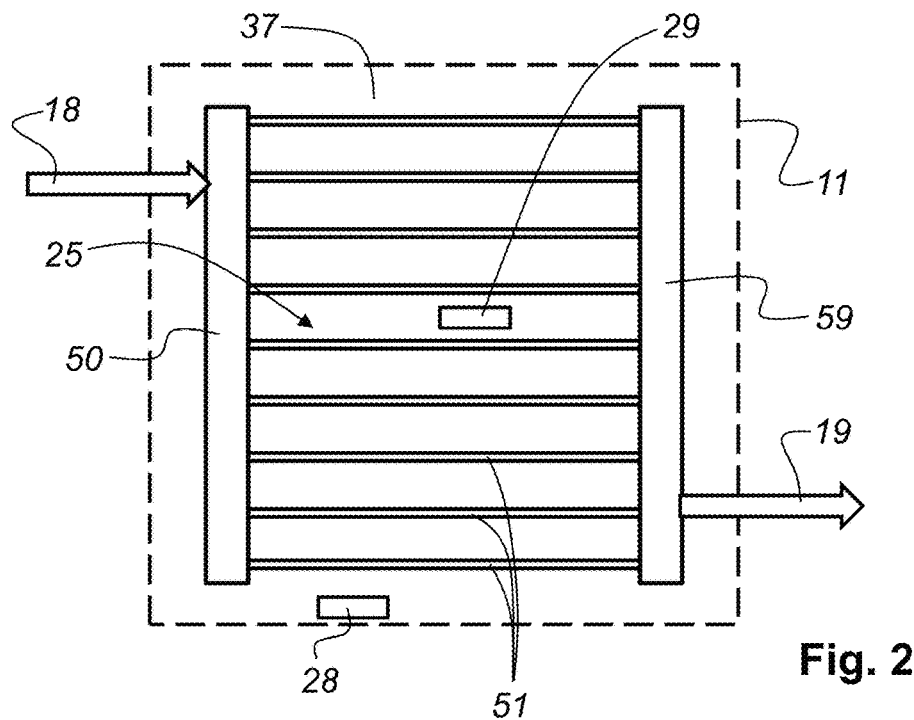
FIG. 2 is a top view of a covering with a means for guiding the plasma or the excited gas or gas mixture, respectively, across the wound area to be treated.

FIG. 2 is a top view of covering 37 showing means 25, which is provided within wound cover 38 to guide plasma P, in accordance with an embodiment of the present invention. In this example embodiment, means 25 includes a plurality of straight distribution channels 51, which lead from distribution element 50 to collection element 59. Distribution element 50 therein is connected with supply port 18 and collection element 59 is connected with removal port 19.

Figure 3:
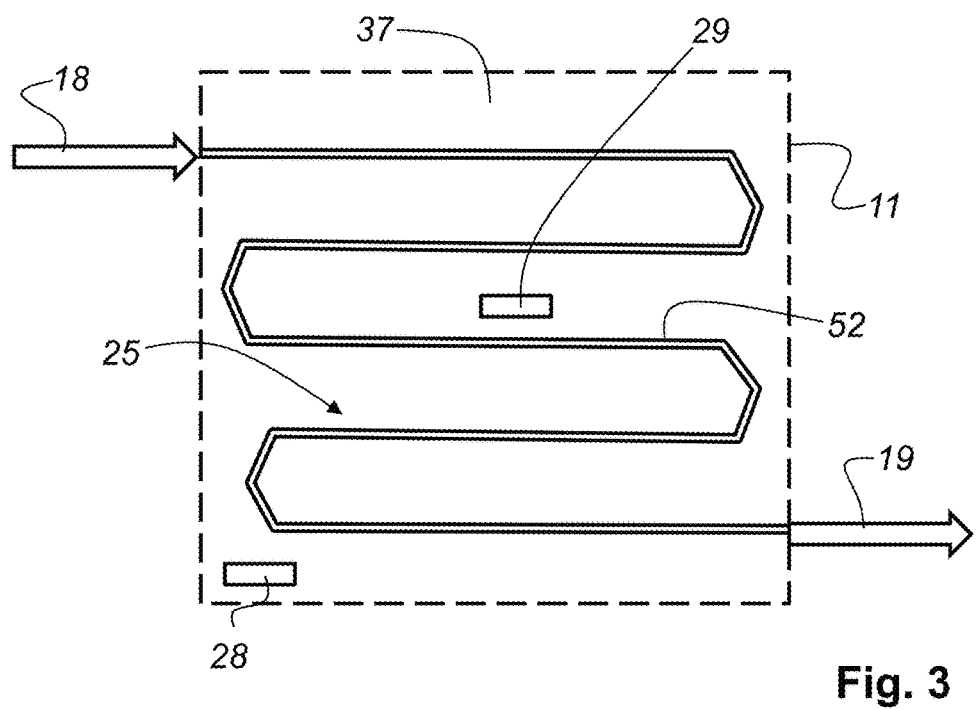
FIG. 3 is top view of a covering with a means for guiding the plasma or the excited gas or gas mixture, respectively, across the wound area to be treated.

FIG. 3 is a top view of covering 37 showing means 25, which is provided within wound cover 38 to guide plasma P, in accordance with an embodiment of the present invention. In this example embodiment, means 25 includes a single meandering conduit 52 that is directly connected to supply port 18 and removal port 19.

Figure 4:
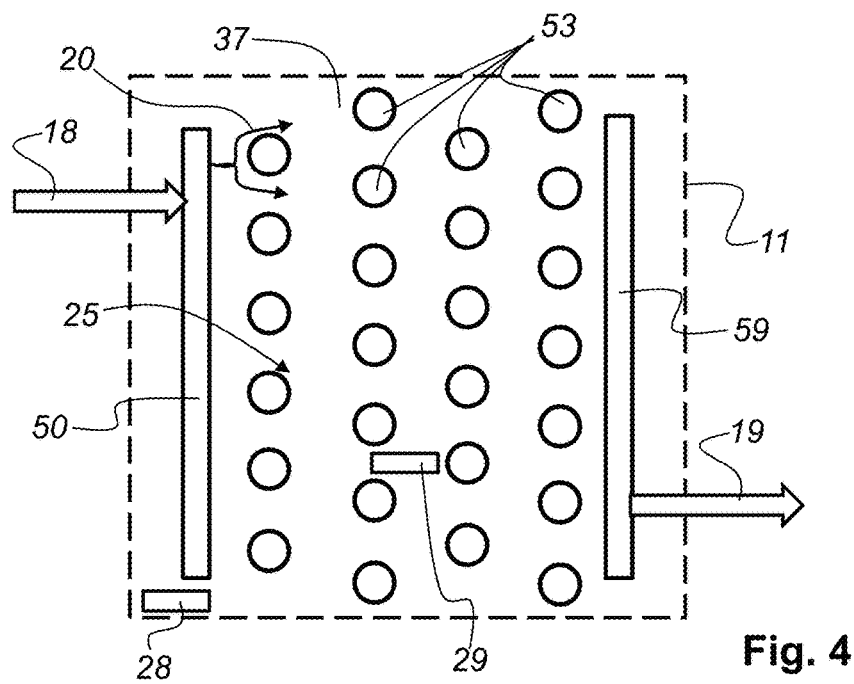
FIG. 4 is a top view of a covering with a means for guiding the plasma or the excited gas or gas mixture, respectively, across the wound area to be treated.

FIG. 4 is a top view of covering 37 showing means 25, which is provided within wound cover 38 to guide plasma P, in accordance with an embodiment of the present invention. In this example embodiment, means 25 includes a plurality of flow obstacles 53. Flow obstacles 53 are arranged as a regular lattice between distribution element 50 and collection element 59. Distribution element 50 is connected to supply port 18 and collection element 59 is connected with removal port 19. Plasma P exits from distribution element 50 and interacts with flow obstacles 53, allowing plasma flow 20 to distribute uniformly on the way to collection element 59.

Figure 5:
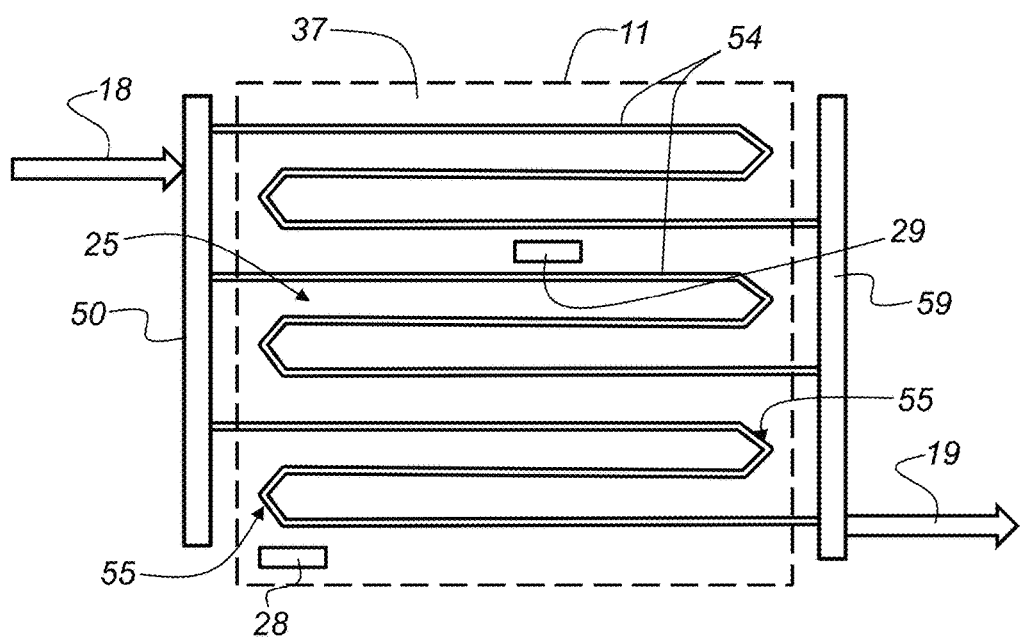
FIG. 5 is a top view of a covering with a means for guiding the plasma or the excited gas or gas mixture, respectively, across the wound area to be treated; and, FIG. 6 is a sectional view of the covering for the wound area, wherein the assignment of the means for guiding the plasma to the wound area to be treated can be seen.

FIG. 5 is a top view of covering 37 showing means 25, which is provided within wound cover 38 to guide plasma P, in accordance with an embodiment of the present invention. In this example embodiment, means 25 includes a plurality of conduits 54, each having two redirections 55. Conduits 54 lead from distribution element 50 to collection element 59. Distribution element 50 is connected with supply port 18, and collection element 59 is connected with removal port 19.

Covering 37 may include RFID-chip 28 to contain electronically stored information about covering 37. For example, plasma generation device 10 can read RFID-chip 28 to identify the type of means 25 in covering 37 and adjust the corresponding settings of plasma generation device 10, via control circuit 3, and/or pump 36 via coupling 27. Covering 37 may also include color sensor 29 to indicate, by a change of color, the status of the treatment. For example, color sensor 29 may be red before treatment begins, turn green during treatment, and turn blue when treatment is complete. RFID-chip 28 and color sensor 29 may be used alone and/or in combination with covering 37.

Figure 6:
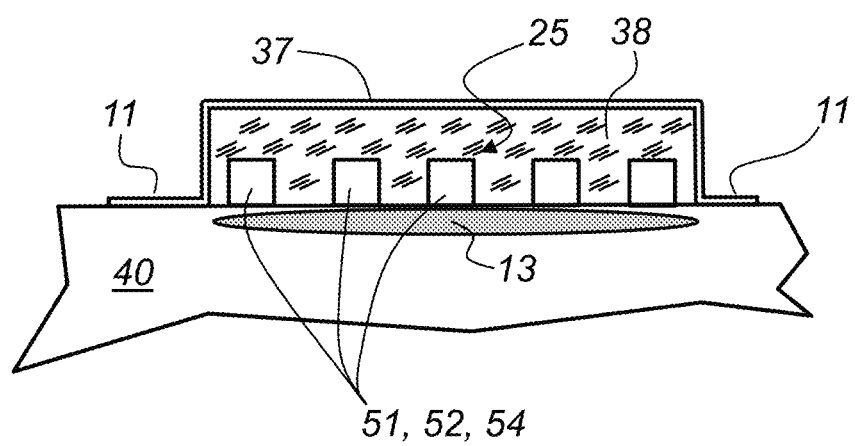

FIG. 6 is a sectional view of covering 37 for wound area 13. Covering 37 encloses wound cover 38 and is glued to body part 40 via circumferential edge 11, such that wound area 13 is enclosed and wound cover 38 lies on the wound area 13. Wound area 38 has a means for guiding plasma P such that plasma P, or the excited gas or gas mixture, enters into interaction with wound area 13 to be treated. Wound cover 38 has at least one distribution channel 51, 52, 54. The distribution channels 51, 52, 54 of wound cover 38 are open towards wound region 13. In order to keep distribution channels 51, 52, 54 free of liquid, they may have a hydrophobic coating. A particularly suitable way of manufacturing distribution channels 51, 52, 54 is to emboss them into the wound area 38.

LIST OF REFERENCE NUMERALS

1 Assembly
3 Control Circuit
4 Electronic Elements
5 Piezoelectric Transformer
6 Gas Line
7 Circuit Board
8 High-Voltage End
10 Plasma Generation Device
11 Circumferential Edge
12 Electric Connection
13 Wound Area
14 Flow Guiding Element
15 Plasma Flow
17 Fan
18 Supply Port
19 Removal Port
20 Plasma Flow
21 First Conduit
22 Second Conduit
23 Cable of Mains Adapter
24 Side of Piezoelectric Transformer
25 Means (guiding)
27 Coupling
28 RFID-Chip
29 Color Sensor
30 Housing
32 Opening
34 Connection Element
35 Control Circuit
36 Pump 37 Covering
38 Wound Cover
40 Body Part
50 Distribution Element
51 Straight Distribution Channels
52 Meandering Distribution Channel
53 Flow Obstacles
54 Distribution Channels with Redirection
59 Collection Element
P Plasma

What is claimed is:

1. An assembly for the treatment of wounds, comprising:
a housing including an opening;
a device including a piezoelectric transformer having a high-voltage end for generating a plasma or an excited gas or gas mixture, respectively, the piezoelectric transformer arranged within the housing such that the high-voltage end is directed towards the opening and the plasma or the excited gas or gas mixture, respectively, is generated in a region of the opening;
a covering including a supply port and a removal port;
a pump;
a coupling arranged to electronically connect the pump with the device;
a first conduit operatively arranged to connect to the device at a first end and the supply port at a second end;
a second conduit operatively arranged to connect to the removal port at a third end and the pump at a fourth end; and,
a wound cover including a means for guiding the plasma or the excited gas or gas mixture, respectively, from the supply port to the removal port, the wound cover operatively arranged between the covering and a wound area such that the plasma is guided across the wound area.

2. The assembly as recited in claim 1, wherein the first conduit comprises a connection element arranged on the first end, wherein the connection element is removably connected to the opening such that the plasma or the excited gas or gas mixture, respectively, generated by the device is transferrable into the first conduit.

3. The assembly as recited in claim 1, wherein the covering comprises a circumferential edge operatively arranged to adhere to a surface such that the covering encloses a wound area.

4. The assembly as recited in claim 1, wherein the means for guiding the plasma or the excited gas or gas mixture, respectively, comprises a plurality of straight distribution channels, each of the plurality of straight distribution channels connect to a distribution element at an inlet end and a collection element at an outlet end, wherein the distribution element is connected to the supply port and the collection element is connected to the removal port.

5. The assembly as recited in claim 4, wherein the plurality of distribution channels comprise a hydrophobic coating.

6. The assembly as recited in claim 1, wherein the means for guiding the plasma or the excited gas or gas mixture, respectively, comprises a single meandering distribution channel connected to the supply port at an inlet end and the removal port at an outlet end.

7. The assembly as recited in claim 6, wherein the single meandering distribution channel comprises a hydrophobic coating.

8. The assembly as recited in claim 1, wherein the means for guiding the plasma or the excited gas or gas mixture, respectively, comprises a plurality of flow obstacles operatively arranged in a regular lattice between a distribution element and a collection element, wherein the distribution element is connected with the supply port and the collection element is connected with the removal port.

9. The assembly as recited in claim 8, wherein the plurality of flow obstacles comprise a hydrophobic coating.

10. The assembly as recited in claim 1, wherein the means for guiding the plasma or the excited gas or gas mixture, respectively, comprises a plurality of distribution channels, each of the plurality of distribution channels comprise two redirections and connect to a distribution element at an inlet end and a collection element at an outlet end, wherein the distribution element is connected to the supply port and the collection element is connected to the removal port.

11. The assembly as recited in claim 10, wherein the plurality of distribution channels comprise a hydrophobic coating.

12. The assembly as recited in claim 1, wherein the means for guiding the plasma or the excited gas or gas mixture, respectively, comprises a structure having pores opening towards the wound area.

13. The assembly as recited in claim 12, wherein the structure comprises a hydrophobic coating.

14. The assembly as recited in claim 1, wherein the covering comprises an RFID-Chip.

15. The assembly as recited in claim 1, wherein the covering comprises a color sensor.

16. The assembly as recited in claim 1, wherein the device is a hand-held device.

* * * * *